(12) United States Patent
Ishikawa et al.

(10) Patent No.: US 8,846,214 B2
(45) Date of Patent: Sep. 30, 2014

(54) AMINE DERIVATIVE AND ORGANIC ELECTROLUMINESCENT ELEMENT

(75) Inventors: Shinichi Ishikawa, Shunan (JP); Naoki Matsumoto, Shunan (JP); Takanori Miyazaki, Shunan (JP); Yasushi Hara, Shunan (JP)

(73) Assignee: Tosoh Corporation, Yamaguchi (JP)

( * ) Notice: Subject to any disclaimer, the term of this patent is extended or adjusted under 35 U.S.C. 154(b) by 8 days.

(21) Appl. No.: 13/375,997

(22) PCT Filed: Jun. 2, 2010

(86) PCT No.: PCT/JP2010/059341

§ 371 (c)(1),
(2), (4) Date: Jan. 26, 2012

(87) PCT Pub. No.: WO2010/140617

PCT Pub. Date: Dec. 9, 2010

(65) Prior Publication Data

US 2012/0112177 A1 May 10, 2012

(30) Foreign Application Priority Data

Jun. 5, 2009 (JP) ................. 2009-136192
Nov. 24, 2009 (JP) ................. 2009-266680

(51) Int. Cl.

| | | |
|---|---|---|
| *H01L 51/54* | (2006.01) | |
| *C07D 213/74* | (2006.01) | |
| *H01L 51/00* | (2006.01) | |
| *C07C 211/61* | (2006.01) | |
| *H05B 33/10* | (2006.01) | |
| *C09K 11/06* | (2006.01) | |
| *H05B 33/14* | (2006.01) | |
| *C07D 333/36* | (2006.01) | |
| *H01L 51/50* | (2006.01) | |

(52) U.S. Cl.
CPC ........... *H01L 51/006* (2013.01); *H01L 51/5088* (2013.01); *C07C 2103/40* (2013.01); *C09K 2211/1011* (2013.01); *C07D 213/74* (2013.01); *C09K 2211/1014* (2013.01); *C07C 211/61* (2013.01); *H05B 33/10* (2013.01); *C09K 11/06* (2013.01); *H01L 2251/552* (2013.01); *C09K 2211/1007* (2013.01); *H05B 33/14* (2013.01); *H01L 51/5048* (2013.01); *C07C 2103/94* (2013.01); *C07D 333/36* (2013.01); *H01L 51/5012* (2013.01); *Y10S 428/917* (2013.01)
USPC ........... 428/690; 428/917; 313/504; 313/505; 313/506; 257/40; 257/E51.05; 257/E51.026; 257/E51.032; 548/304.1; 548/418; 548/440; 548/444; 546/18; 546/24; 546/81; 546/101; 564/26; 564/426; 564/434

(58) Field of Classification Search
USPC .................. 428/690, 917; 313/504, 505, 506; 257/40, E51.05, E51.026, E51.032; 548/418, 440, 304.1, 444; 564/26, 426, 564/434; 546/18, 24, 81, 101
See application file for complete search history.

(56) References Cited

U.S. PATENT DOCUMENTS

| | | | |
|---|---|---|---|
| 6,849,348 B2 | 2/2005 | Zheng et al. | |
| 7,348,071 B2 | 3/2008 | Zheng et al. | |
| 7,838,130 B2 | 11/2010 | Takashima et al. | |
| 7,994,316 B2 | 8/2011 | Yamakawa et al. | |
| 2004/0131880 A1 | 7/2004 | Zheng et al. | |
| 2004/0241496 A1 | 12/2004 | Zheng et al. | |
| 2009/0184312 A1* | 7/2009 | Nishiyama et al. | ............. 257/40 |
| 2009/0267491 A1 | 10/2009 | Takashima et al. | |
| 2010/0249406 A1 | 9/2010 | Yamakawa et al. | |
| 2011/0190494 A1 | 8/2011 | Aihara et al. | |
| 2011/0288295 A1 | 11/2011 | Aihara et al. | |

FOREIGN PATENT DOCUMENTS

| | | |
|---|---|---|
| JP | 2008-50337 A | 3/2008 |
| JP | 2008-115093 A | 5/2008 |
| JP | 2008-201769 A | 9/2008 |
| JP | 2010-64963 A | 3/2010 |
| JP | 2010-70495 A | 4/2010 |
| WO | 2004/061048 A1 | 7/2004 |
| WO | 2007/119800 A1 | 10/2007 |

OTHER PUBLICATIONS

U.S. Appl. No. 13/391,046 to Hidenori Aihara et al., filed Feb. 17, 2012.
"International Search Report (ISR).", Application No. PCT/JP2010/059341, Date: Jun. 29, 2010, pp. 1-2.
Diarmuid F. O'Brien et al., "Hole Transporting Materials with High Glass Transition Temperatures for Use in Organic Light-Emitting Devices", Advanced Materials (Germany), vol. 10, No. 14., Jun. 3, 1998, pp. 1108-1112.
Yasuhiko Shirota et al., "Starburst Molecules Based on n-electron Systems as Materials for Organic Electroluminescent Devices", Journal of Luminescence (Netherland), vol. 72, No. 74., 1997, pp. 985-991.

* cited by examiner

*Primary Examiner* — Gregory Clark
(74) *Attorney, Agent, or Firm* — Greenblum & Bernstein, P.L.C.

(57) ABSTRACT

An amine derivative represented by the following general formula (1) and exhibiting a temperature difference of 30° C. or more as defined by the difference of [decomposition temperature (° C.) minus sublimation temperature (° C.)]:

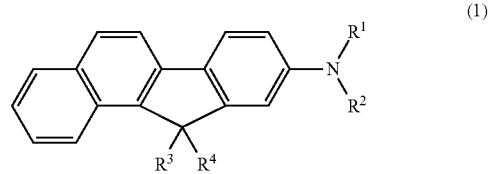

(1)

wherein $R^1$ and $R^2$ independently represent a substituted or unsubstituted $C_{6-40}$ aryl or $C_{5-40}$ heteroaryl group; and $R^3$ and $R^4$ independently represent a hydrogen atom, a straight-chain, branched or cyclic $C_{1-18}$ alkyl or $C_{1-18}$ alkoxy group, or a substituted or unsubstituted $C_{6-40}$ aryl or $C_{5-40}$ heteroaryl group, provided that $R^3$ and $R^4$ may form together a cyclic hydrocarbon group. The amine derivative is useful as an organic electroluminescent material.

4 Claims, No Drawings

AMINE DERIVATIVE AND ORGANIC ELECTROLUMINESCENT ELEMENT

TECHNICAL FIELD

This invention relates to a novel amine derivative having a benzofluorene group, and a organic electroluminescent (EL) device utilizing the amine derivative.

The novel amine derivative according to the present invention can be used as a photosensitive material and an organic photoconductive material and, more specifically, as a hole transport material, a hole injection material and an emitting material in an organic electroluminescent device for use in a flat panel light source or display, and in an electrophotographic photoreceptor and other devices.

BACKGROUND ART

At present, a wide spread attention is attracted to an organic electroluminescent device for next-generation flat panel displays, and such organic electroluminescent device is now being utilized for a sub-display of cell phones and others. An organic electroluminescent device (which is hereinafter referred to "organic EL device" when appropriate) has a multilayer structure comprising a hole transport layer, an emitting layer and an electron transport layer, which are sandwiched between a cathode and an anode. At present, a multilayer having a similar arrangement but additionally having a hole injection layer between the cathode and the hole transport layer, and an electron injection layer between the anode and the electron transport layer is widely adopted to reduce power consumption of the organic EL device and prolong life time thereof.

As a hole transport material, triarylamine derivatives having a diamine structure such as, for example, 4,4'-bis[N-(1-naphthyl)-N-phenylamino]biphenyl (α-NPD) and N,N,N',N'-tetra[(1,1'-biphenyl)-4-yl]benzidine (TBDB) were reported (see, for example, Advanced Materials, Germany, 1998, Vol. 10, No. 14, p 1108-1112, FIG. 1 and Table 1; and Journal of Luminescence, Netherland, 1997, 72-74, p 985-991, FIG. 1).

In recent years, development of new organic emitting materials is eagerly desired for more enhancing the efficiency and life time of an organic EL device.

An organic electroluminescent material having a benzofluorene structure has been proposed in, for example, WO 2004/61048, claims). However, this patent document is silent on a compound having a benzofluorene structure to which an amino group has been directly bonded. This patent document describes that a polymeric material having a benzofluorene group is useful as an emitting material, but teaches nothing about the use of such polymeric material as a hole transport material and a hole injection material.

Various structures are known for amine compounds having a benzofluorene structure (see, for example, JP 2008-50337 A, claims; and JP 2008-201769, claims). However, an amine derivative represented by the general formula (1), shown below, is not known and processing properties of the amine derivative of formula (1) which are important for producing an organic EL device by a vacuum deposition method are not suggested in these patent documents.

PRIOR ART DOCUMENT

Patent Document

Patent document 1: WO 2004/61048, claims
Patent document 2: JP 2008/50337 A, claims
Patent document 3: JP 2008-201769 A, claims Non-Patent Document Non-patent Document 1: Advanced Materials, Germany, 1998, Vol. 10, No. 14, p 1108-1112, FIG. 1 and Table 1
Non-patent Document 2: Journal of Luminescence, Netherland, 1997, 72-74, p 985-991, FIG. 1

SUMMARY OF THE INVENTION

Problems to Be Solved by the Invention

An object of the present invention is to provide an organic electroluminescent material which gives an organic EL device exhibiting an enhanced power efficiency and a long life time as compared with heretofore known organic electroluminescent materials, and which is suitable for forming by a vacuum deposition method or other methods. More specifically, an object of the present invention is to provide a novel amine derivative having a specific benzofluorene substituent which is useful as a hole injection material, a hole transport material and an emitting material which are used in an organic electroluminescent device and others.

Another object of the present invention is to provide an organic electroluminescent device having at least one layer selected from an emitting layer, a hole transport layer and a hole injection layer, which layers are made of the above-mentioned amine derivative.

The present inventors made an extensive research and found that a specific amine derivative represented by the formula (1) gives an organic EL device exhibiting high power efficiency and long life time as compared with those made of the heretofore known organic electroluminescent materials, and exhibits enhanced durability at processing for producing an organic EL device. Based on these findings, the present invention has been completed.

In one aspect of the present invention, there is provided an amine derivative represented by the following general formula (1) and exhibiting a temperature difference of 30° C. or more as defined by the difference of [decomposition temperature (° C.) minus sublimation temperature (° C.)]:

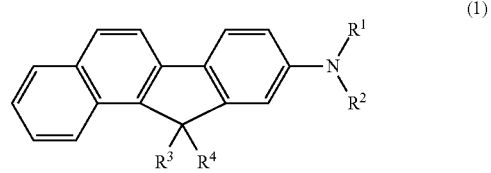

(1)

wherein $R^1$ and $R^2$ may be the same or different and represent a substituted or unsubstituted aryl group having 6 to 40 carbon atoms or a substituted or unsubstituted heteroaryl group having 5 to 40 carbon atoms; and $R^3$ and $R^4$ may be the same or different and represent a hydrogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 40 carbon atoms or a substituted or unsubstituted heteroaryl group having 5 to 40 carbon atoms, provided that $R^3$ and $R^4$ may form a cyclic hydrocarbon group having 3 to 8 carbon atoms together with the carbon atom in the benzofluorene structure to which $R^3$ and $R^4$ are bonded.

In another aspect of the present invention, there is provided an organic electroluminescent device characterized by having at least one layer selected from an emitting layer, a hole transport layer and a hole injection layer, which layers are made of the above-mentioned amine derivative.

In still another aspect of the present invention, there is a process for producing an organic electroluminescent device characterized by making at least one layer selected from an emitting layer, a hole transport layer and a hole injection layer, wherein said at least one layer is made by forming a thin film by a vacuum deposition method from the above-mentioned amine derivative.

Effect of the Invention

The amine derivative of the present invention represented by the general formula (1) gives an organic electroluminescent device which can be operated with a low voltage and a high power efficiency. Therefore, the amine derivative is suitable for a hole injection material, a hole transport material and an emitting material, which are used in an organic EL device and an electrophotographic photoreceptor and other devices.

MODES FOR CARRYING OUT THE INVENTION

The invention will now be described in detail. In the general formula (1) representing the amine derivative according to the present invention, $R^1$ and $R^2$ may be the same or different and independently represent a substituted or unsubstituted aryl group having 6 to 40 carbon atoms or a substituted or unsubstituted heteroaryl group having 5 to 40 carbon atoms.

As specific examples of the aryl group having 6 to 40 carbon atoms, there can be mentioned a phenyl group, a naphthyl group, a biphenylyl group, an anthryl group, a fluorenyl group, a phenathryl, a pyrenyl group, a chrysenyl group, a perylenyl group, a picenyl group, a benzo[a]fluorenyl group, a benzo[b]fluorenyl group and a benzo[c]fluorenyl group. The aryl group having 6 to 40 carbon atoms is not particularly limited to these aryl groups. These aryl groups may have a substituent or substituents. In view of high stability for forming the amine derivative by a vacuum deposition method, a substituted or unsubstituted aryl group having 6 to 18 carbon atoms is preferable.

The heteroaryl group having 5 to 40 carbon atoms is a group of an aromatic ring containing at least one hetero atom selected from an oxygen atom, a nitrogen atom and a sulfur atom, and, as specific examples thereof, there can be mentioned a quinolyl group, a pyridyl group, a furyl group, a thienyl group, an oxazolyl group, a thiazolyl group, a benzoxazolyl group and a benzo-imidazolyl group. The heteroaryl group having 5 to 40 carbon atoms is not particularly limited to these heteroaryl groups. These heteroaryl groups may have a substituent or substituents, similarly to the above-mentioned aryl groups. In view of high stability for forming the amine derivative by a vacuum deposition method, a substituted or unsubstituted heteroaryl group having 5 to 18 carbon atoms is preferable.

In the general formula (1) representing the amine derivative according to the present invention, $R^3$ and $R^4$ independently represent a hydrogen atom, a straight-chain, branched or cyclic alkyl group having 1 to 18 carbon atoms, a straight-chain, branched or cyclic alkoxy group having 1 to 18 carbon atoms, a substituted or unsubstituted aryl group having 6 to 40 carbon atoms or a substituted or unsubstituted heteroaryl group having 5 to 40 carbon atoms, provided that $R^3$ and $R^4$ may form a cyclic hydrocarbon group having 3 to 8 carbon atoms together with the carbon atom in the benzofluorene structure to which $R^3$ and $R^4$ are bonded.

As specific examples of the straight-chain, branched or cyclic alkyl group having 1 to 18 carbon atoms, there can be mentioned a methyl group, an ethyl group, a propyl group, an isopropyl group, a butyl group, a sec-butyl group, a tert-butyl group, a pentyl group, a hexyl group, a heptyl group, an octyl group, a stearyl group, a trichloromethyl group, a trifluoromethyl group, a cyclopropyl group, a cyclohexyl group, a 1,3-cyclohexadienyl group and a 2-cyclopenten-1-yl group. In view of high stability for forming the amine derivative by a vacuum deposition method, a substituted or unsubstituted alkyl group having 1 to 6 carbon atoms is preferable.

As specific examples of the straight-chain, branched or cyclic alkoxy group having 1 to 18 carbon atoms, there can be mentioned a methoxy group, an ethoxy group, a propoxy group, an isopropoxy group, a n-butoxy group, a sec-butoxy group, a tert-butoxy group, a pentyloxy group, a hexyloxy group, a stearyloxy group and a trifluoromethoxy group. In view of high stability for forming the amine derivative by a vacuum deposition method, a substituted or unsubstituted alkoxy group having 1 to 6 carbon atoms is preferable.

As specific examples of the aryl group having 6 to 40 carbon atoms and the heteroaryl group having 5 to 40 carbon atoms for $R^3$ and $R^4$, there can be mentioned those which are recited for the above-mentioned $R^1$ and $R^2$. In view of high stability for forming the amine derivative by a vacuum deposition method, a substituted or unsubstituted aryl group having 6 to 18 carbon atoms and a substituted or unsubstituted heteroaryl group having 5 to 18 carbon atoms are preferable.

$R^3$ and $R^4$ may form a cyclic hydrocarbon group having 3 to 8 carbon atoms together with the carbon atom in the benzofluorene structure to which $R^3$ and $R^4$ are bonded. The cyclic hydrocarbon group preferably includes a cyclohexylidene group having 3 to 8 carbon atoms such as, for example, cyclohexylidene group and a cyclohexyl group.

As preferable specific examples of the substituent or substituents, which $R^1$, $R^2$, $R^3$ and $R^4$ may have, there can be mentioned a halogen atom, a straight-chain, branched or cyclic alkyl group having 1 to 10 carbon atoms and a straight-chain, branched or cyclic alkoxy group having 1 to 10 carbon atoms.

As specific examples of the amine derivative according to the present invention, those which are expressed by the following chemical structures can be mentioned. The amine derivative is not limited thereto.

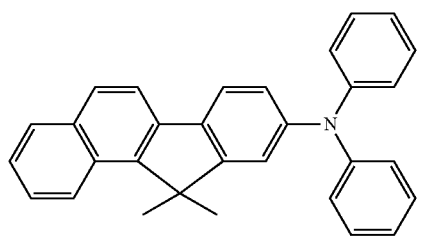

1-1

1-2
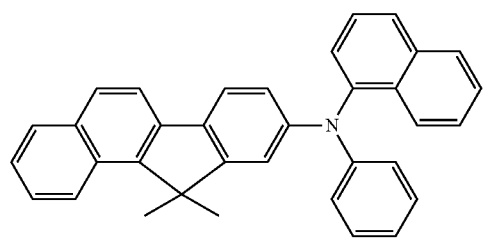
1-3
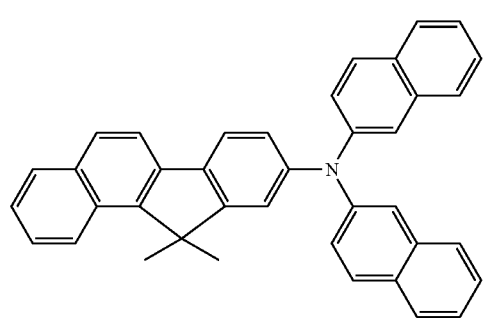
1-4
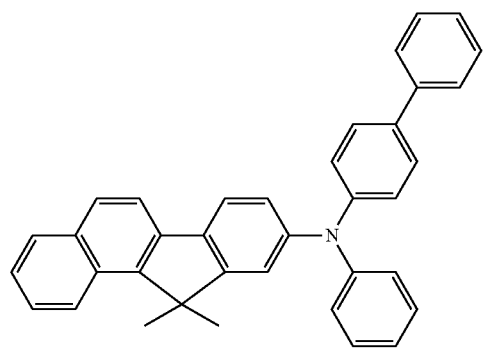
1-5
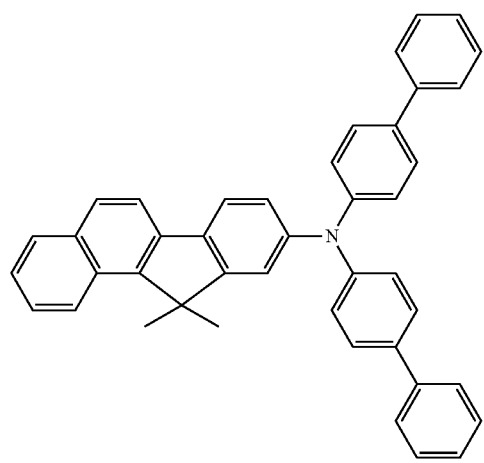
1-6
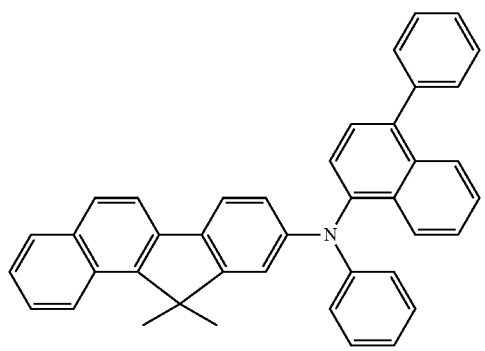
1-7
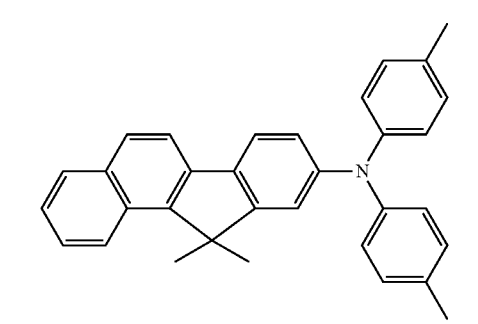
1-8
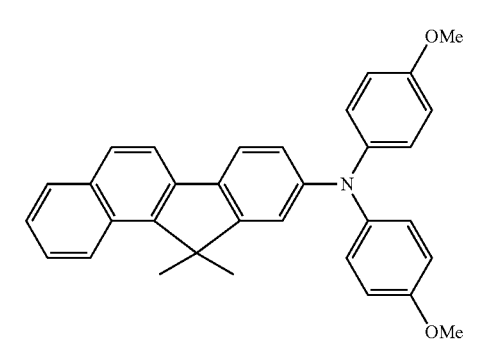
1-9
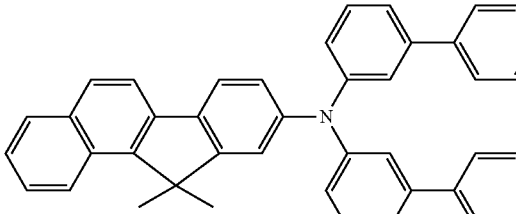
1-10
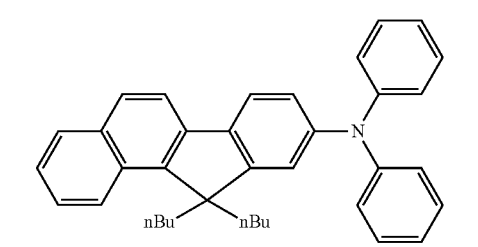

1-11
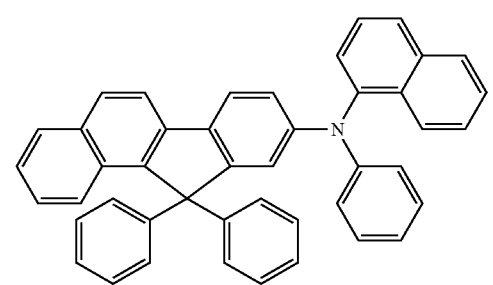
1-12
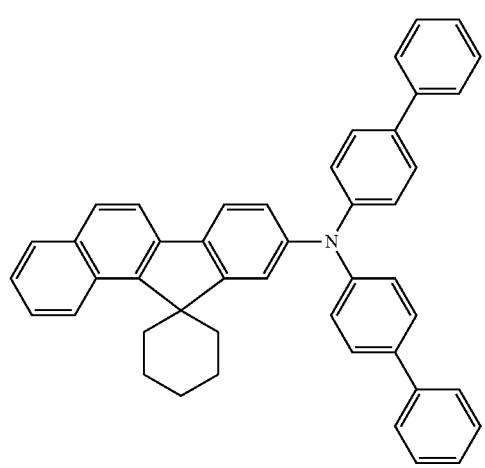
1-13
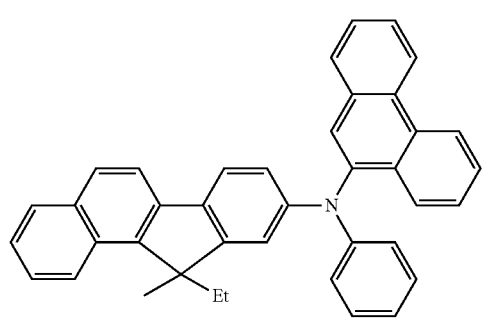
1-14
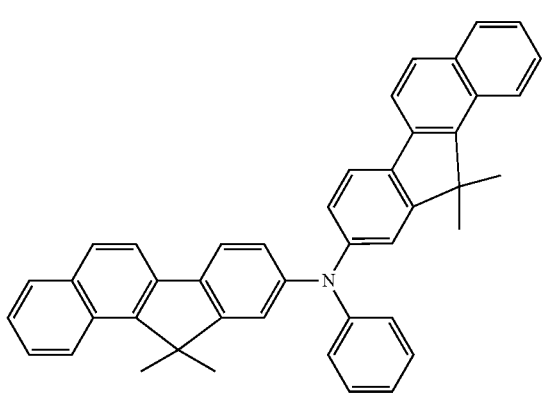
1-15
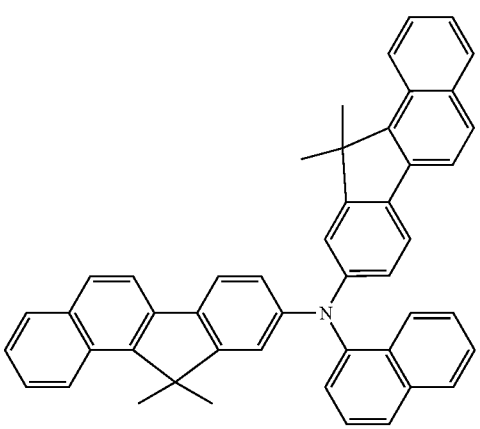
1-16
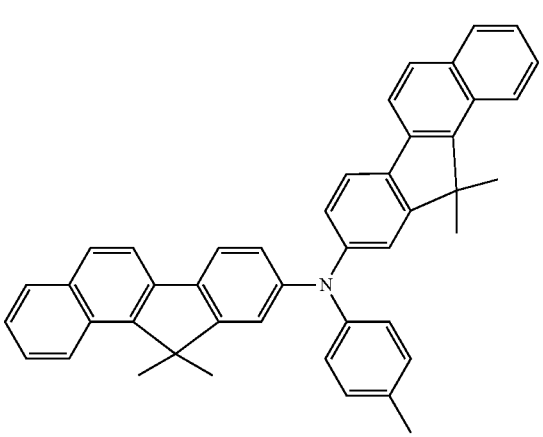
1-17
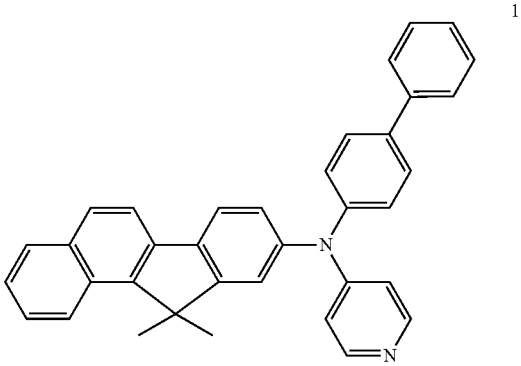
1-18
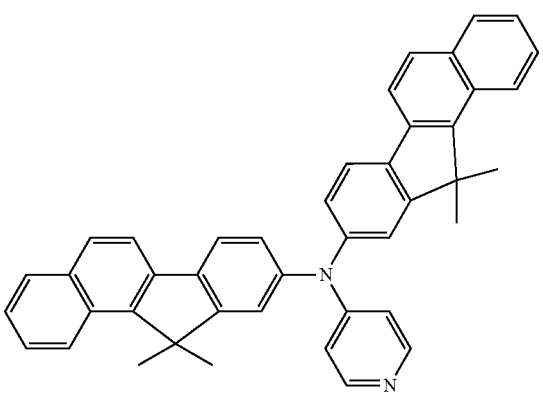

1-19

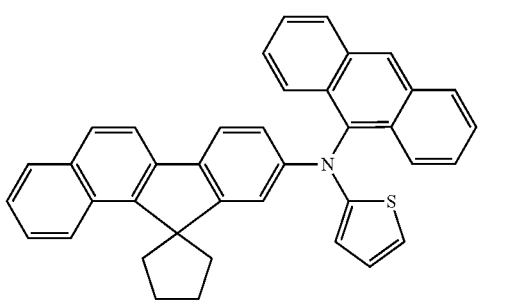

1-20

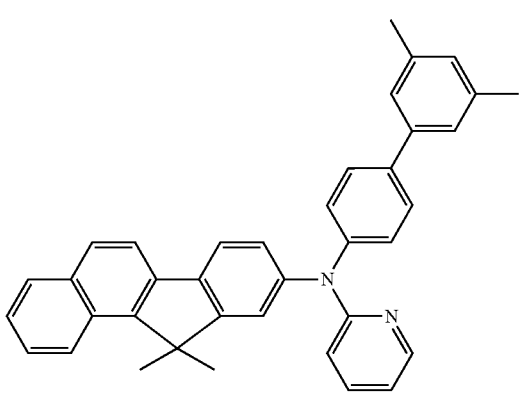

1-21

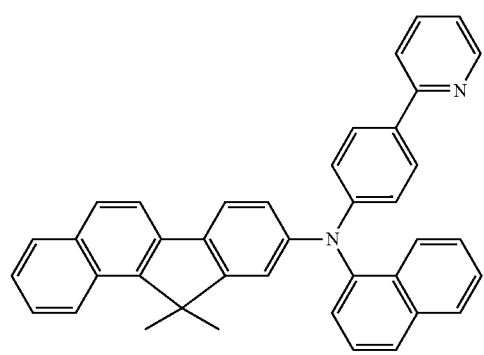

The amine derivative according to the present invention can be synthesized by, for example, the known methods, which include an amination method as described in, for example, non-patent document 3: Tetrahedron Letters, 1998, vol. 39, P 2367.

A representative method for synthesis includes, for example, an amination method represented by the following reaction scheme wherein a benzofluorene derivative represented by the following general formula (2) (where X represents a halogen atom) is reacted with a secondary amine represented by the following formula (3) to give the amine derivative represented by the formula (1).

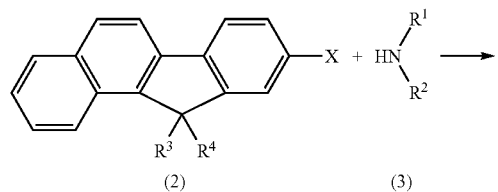

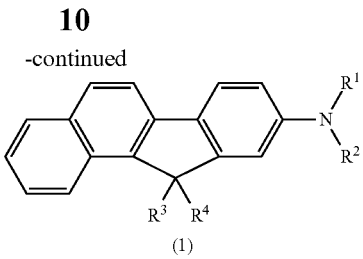

(1)

The synthesized amine derivative can be obtained with a purity of at least 99.9% by adopting a purifying method such as, for example, chromatography, recrystallization or sublimation. When an amine derivative having an especially high purity is required, purification by sublimation is preferable. However, an amine derivative having a sublimation temperature and a decomposition temperature, which are in close proximity to each other, is difficult to purify by sublimation into a high purity because the sublimation procedure is accompanied by decomposition to some extent. To minimize undesirable decomposition of the amine derivative which occurs in the process of making a thin film layer from the amine derivative, the amine derivative must have a sublimation temperature and a decomposition temperature, which are apart from each other to some extent. More specifically the amine derivative exhibits a temperature difference of 30° C. or more as defined by the difference of [decomposition temperature (° C.) minus sublimation temperature (° C.)]. Preferably the temperature difference as defined by the difference of [decomposition temperature (° C.) minus sublimation temperature (° C.)] is at least 50° C.

The amine derivative according to the present invention preferably exhibits an energy level difference of at least 3.0 (eV) as defined by the energy level difference of [LUMO (eV) minus HOMO (eV)]. In the frontier orbital theory, the HOMO (highest occupied molecular orbital) refers to a molecular orbital exhibiting a highest energy level among the molecular orbitals occupied by electrons, and the LUMO (lowest unoccupied molecular orbital) refers to a molecular orbital exhibiting a lowest energy level among the molecular orbitals unoccupied by electrons. The performance of an organic electroluminescent device varies depending upon not only the energy level difference of [LUMO minus HOMO], but also other factors. It is to be noted, however, that, when the energy level difference of [LUMO minus HOMO] is larger, adaptabilities of the amine derivative to devices of various different colors, and as a fluorescent material and a phosphorescent material are more enhanced.

In the case when an organic electroluminescent device made from the amine derivative is used for panels provided in an automobile, the device is required to have a high heat resistance in consideration of the temperature elevation in an automobile at daytime in summer. Thus, the amine derivative preferably has a glass transition temperature of at least 120° C.

EXAMPLES

The invention will now be described in more detail by the following examples, but it is by no means limited to these examples.

The following analytical instruments and measuring methods were adopted in the examples.

(Elementary Analysis)

Elemental analyzer: PerkinElmer fully automatic elemental analyzer 2400 II

Oxygen flask burning—IC measurement method: ion chromatograph IC-2001 available from Tosoh Corporation (Mass Spectrometry)

Mass spectrometer: M-80B available from Hitachi Ltd.

Measurement method: Field desorption mass spectrometry (FD-MS)

(HOMO measurement)

Measurement of HOMO according to cyclic voltammetry was carried out by the following method and instrument.

Measurement instrument: HA-501 and HB-104, available from Hokuto Denko Corporation.

Measurement Method:

Working electrode: Glassy carbon electrode

Counter electrode: Platinum electrode

Reference electrode: Ag/Ag$^+$

Supporting electrolyte: Tetra-n-butylammonium perchlorate

Solvent: Dichloromethane (LUNO Measurement)

Measurement of LUMO was carried out by the following method and instrument.

Measurement instrument: Ultraviolet and visible spectrophotometer U-2010 available from Hitachi Ltd.

Measurement Method:

Solvent: tetrahydrofuran

Solution concentration $10^{-5}$ mol/l (Glass Transition Temperature Measurement)

Measurement Instrument:

DSC-3100 available from McScience Inc.

Measurement method: Reference sample: $Al_2O_3$ 5.0 mg

Temperature Elevation Rate:

10° C./min in nitrogen atmosphere (HPLC Analysis)

Measurement instrument: Multi-station LC-8020 available from Tosoh Corporation

Measurement Method: Column:

Inertsil ODS-3V, 4.6 mmΦ×250 mm

Detector: UV detection, wavelength 254 nm

Eluent: Methanol/tetrahydrofuran 9/1 (v/v) mixed liquid (Decomposition Temperature Measurement)

Measurement Instrument:

System 8100 available from Rigaku Corporation Measurement method: Reference sample:

$Al_2O_3$ 5.0 mg

Temperature elevation rate: 10° C./min in nitrogen atmosphere (Sublimation Temperature Measurement)

Measurement Instrument:

Organic material sublimation purifying apparatus P-150 available from ALS Technology Co., Ltd.

Measurement method:

Sublimation pressure: $<10^{-3}$ Pa,

Sublimation temperature was measured by visual inspection

Synthesis Example 1

Synthesis of Compound A

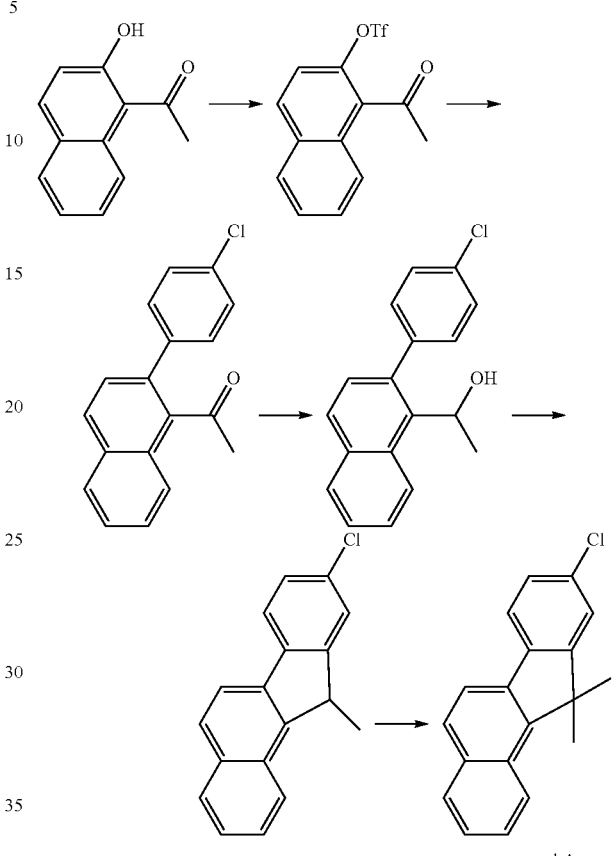

compound A

A 300 ml eggplant flask was charged with 18.6 g (100 mmol) of 2'-hydroxy-1'-acetonaphthone (available from Wako Pure Chemical Industries Ltd.), 100 ml of dichloromethane (available from Kanto Chemical Co., Inc.) and 39.6 g (500 mmol) of pyridine (available from Kishida Chemical Co., Ltd.). The liquid reaction mixture was cooled to below 5° C. 31.0 g (110 mmol) of trifluoromethanesulfonic anhydride (available from Wako Pure Chemical Industries Ltd.) was dropwise added while the reaction temperature was controlled so as not to exceed 5° C. The reaction mixture was stirred at room temperature overnight. Water was added to the liquid reaction mixture to quench the reaction and effect phase separation. An obtained organic phase was washed with an aqueous 3.5% hydrochloric acid solution and then with water, and then, dried over anhydrous magnesium sulfate and concentrated. The thus-obtained 32.7 g of 1'-acetonaphthone-2'-trifluoromethanesulfonate was isolated as slightly yellow oily material. This product was used as it was without purification for the succeeding reaction.

A 500 ml eggplant flask was charged with 15.1 g (47.5 mmol) of the obtained 1'-acetonaphthone-2'-trifluoromethanesulfonate, 7.8 g (50.0 mmol) of 4-chlorophenylboronic acid (available from Tokyo Chemical Industry Co., Ltd.), 549 mg (0.475 mmol) of tetrakis(triphenylphosphine) palladium (available from Aldrich Chemical Co., Inc.), 100.7 g of an aqueous 20 wt. % sodium carbonate solution and 250 ml of tetrahydrofuran (available from Kanto Chemical Co., Inc.). The liquid mixture was heated and stirred at 60° C.

overnight. The thus-obtained liquid reaction mixture was cooled to room temperature to effect phase separation. An obtained organic phase was washed with water, and then, dried over anhydrous magnesium sulfate and concentrated. Thus 12.4 g of a light yellow crystal was obtained. $^1$H-NMR analysis revealed that the light yellow crystal was target 2'-(4-chlorophenyl)-1'-acetonaphthone. This product was used as it was without purification for the succeeding reaction.

$^1$H-NMR(200 MHz, CDCl$_3$): 2.12 (3H, s), 7.33-7.65 (7H, m), 7.78-8.01 (3H, m)

$^{13}$C-NMR(50 MHz, CDCl$_3$): 32.9, 124.7, 126.5, 127.1, 127.6, 128.3, 128.8, 128.9, 129.5, 130.6, 132.6, 134.3, 134.4, 138.4, 138.7, 207.1

A 300 ml eggplant flask was charged with 9.8 g (35 mmol) of the obtained 2'-(4-chlorophenyl)-1'-acetonaphthone, 70 ml of tetrahydrofuran (available from Kanto Chemical Co., Inc.) and 70 ml of ethanol (available from Kanto Chemical Co., Inc.). The liquid mixture was dissolved, and then, 6.6 g (175 mmol) of sodium boron hydride (available from Kishida Chemical Co., Ltd.) was added to the solution. The solution was stirred at room temperature for 8 hours.

Then 100 g of an aqueous 10% ammonium chloride solution was added to the solution while care was taken so as not to form foam. The liquid reaction mixture was concentrated under a reduced pressure. The obtained residue was subjected to extraction with 200 ml of toluene. The extracted material was washed with water, and then dried over anhydrous magnesium sulfate and concentrated to give 9.4 g of a light yellow crystal. $^1$H-NMR analysis revealed that the light yellow crystal was target 1-(1-hydroxy)ethyl-2(4-chlorophenyl)naphthalene. This product was used as it was without purification for the succeeding reaction.

$^1$H-NMR (200 MHz, CDCl$_3$): 1.71 (3H, d, J=7. 0 Hz),2.05 (1H, br-s), 5.35(1H, q, J=7.0 Hz), 7.16-7.63 (7H, m), 7.69-7.95 (2H, m), 8.76-8.93 (1H, br-d)

$^{13}$C-NMR (50 MHz, CDCl$_3$): 23.9, 68.9, 125.8, 125.9, 127.0, 127.8, 127.9, 128.4, 128.8, 130.4, 130.8, 133.2, 134.2, 136.9, 137.1, 140.6

A 100 ml eggplant flask was charged with 2.8 g (10 mmol) of the obtained 1-(1-hydroxy)ethyl-2-(4-chlorophenyl)naphthalene and 20 ml of chloroform (available from Kanto Chemical Co., Inc.). The reaction mixture was cooled to 0° C., and then, 1.85 g (13 mmol) of trifluoroboron diethyletherate (available from Kanto Chemical Co., Inc.) was dropwise added to the reaction mixture. The reaction mixture was stirred at room temperature for 1 hour.

Then 20 g of water was added to the reaction mixture to quench the reaction and effect phase separation. Then an organic phase, obtained by the phase separation, was washed with water and then dried over anhydrous magnesium sulfate and concentrated to give 2.7 g of a light yellow solid. $^1$H-NMR analysis revealed that the light yellow solid was target 9-chloro-11-methyl-11H-benzo[a]fluorine. This product was used as it was without purification for the succeeding reaction.

$^1$H-NMR (200 MHz, CDCl$_3$): 1.66 (3H, d, J=7.2 Hz), 4.33 (1H, q, J=7.2 Hz), 7.32-7.65(5H, m), 7.70 (1H, d, J=8.1 Hz), 7.80-8.01 (3H, m), 8.06 (1H, d, J=8.0 Hz)

Then 2.7 g (10 mmol) of the obtained 9-chloro-11-methyl-11H-benzo[a]fluorine, 2.3 g (10 mmol) of benzyltriethylammonium chloride (available from Kishida Chemical Co., Ltd.) and 4.3 g (30 mmol) of methyl iodide (available from Kanto Chemical Co., Inc.) were dissolved in 20 ml of dimethylsulfoxide (available from Wako Pure Chemical Industries Ltd.). The obtained solution was cooled to 0° C., and then, an aqueous 48% solution of sodium hydroxide 1.2 g (30 mmol) was dropwise added while being stirred. The obtained reaction mixture was stirred at room temperature for 1 hour, and then 50 ml of toluene (available from Kanto Chemical Co., Inc.) was added thereto to effect phase separation. An organic phase, obtained by the phase separation, was washed with water and then dried over anhydrous magnesium sulfate. A liquid extract obtained from the dried product was concentrated to give a light yellow crystal. The light yellow crystal was subjected to silica gel column chromatography using hexane as eluent to give 2.0 g of a white crystal of target 9-chloro-11,11-dimethyl-11H-benzo[a]fluorine (compound A) (yield: 72%).

$^1$H-NMR (200 MHz, CDCl$_3$): 1.73 (6H, s), 7.21-7.66 (5H, m), 7.69 (1H, d, J=7.8 Hz), 7.80-7.99 (3H, m), 8.19 (1H, d, J=8.3 Hz)

$^{13}$C-NMR (50 MHz, CDCl$_3$): 26.3, 48.8, 118.6, 120.6, 122.8, 124.0, 125.0, 126.2, 127.2, 128.7, 130.0, 132.7, 134.0, 135.6, 137.8, 147.1, 157.0

Example 1

Synthesis of Compound 1-4

In a nitrogen atmosphere, a 500 ml flask equipped with a stirrer was charged with 27.9 g (0.30 mol) of aniline (available from Kishida Chemical Co., Ltd.), 23.3 g (0.10 mol) of 4-bromobiphenyl (available from Wako Pure Chemical Industries Ltd.), 14.4 g (0.15 mol) of sodium-tert-butoxide (available from Kanto Chemical Co., Inc.), 450 mg (2.0 mmol) of palladium acetate (available from Kishida Chemical Co., Ltd.), 1.6 g (8.0 mmol) of tri-tert-butylphosphine (available from Aldrich Chemical Co., Inc.) and 300.0 g of o-xylene (available from Kishida Chemical Co., Ltd.). The charged mixture was stirred at 130° C. for 10 hours. After completion of the reaction, 50 ml of distilled water was added to the reaction mixture, and the reaction mixture was stirred at room temperature for 0.5 hour and allowed to leave to effect phase separation. An aqueous phase was removed. Then an obtained organic layer was washed with an aqueous saturated sodium chloride solution, and phase separation was effected and an aqueous phase was removed. Then the organic layer was concentrated under a reduced pressure, and o-xylene as solvent was distilled off. The thus-obtained residue was subjected to silica gel column chromatography to give 23.1 g of a white solid with a purity of 99.9% in a yield of 94%.

Mass analysis and elemental analysis revealed that the obtained white solid was N-phenyl-N-4-biphenylylamine.

Mass analysis (FDMS): 245 (M$^+$)

Elemental analysis (calculated): C=88.1, H=6.2 and N=5.7

Elemental analysis (found): C=88.0, H=6.2 and N=5.8

In a nitrogen atmosphere, a 500 ml flask equipped with a stirrer was charged with 12.2 g (50 mmol) of the obtained N-phenyl-N-4-biphenylylamine, 14.0 g (50 mmol) of the compound A synthesized in Synthesis Example 1, 5.8 g (60 mmol) of sodium-tert-butoxide (available from Kanto Chemical Co., Inc.), 225 mg (1.0 mmol) of palladium acetate (available from Kishida Chemical Co., Ltd.), 0.8 g (4.0 mmol) of tri-tert-butylphosphine (available from Aldrich Chemical Co., Inc.) and 100.0 g of o-xylene (available from Kishida Chemical Co., Ltd.). The charged mixture was stirred at 140° C. for 10 hours. After completion of the reaction, 50 ml of distilled water was added to the reaction mixture, and the reaction mixture was stirred at room temperature for 0.5 hour and allowed to leave to effect phase separation. An aqueous phase was removed. Then an obtained organic layer was washed with an aqueous saturated sodium chloride solution, and an aqueous phase was removed. Then the organic layer was concentrated under a reduced pressure and o-xylene as solvent was distilled off. The obtained residue was subjected to silica gel column chromatography to give 21.7 g of a light yellow solid with a purity of 99.9% in a yield of 89%.

Mass analysis and elemental analysis revealed that the obtained light yellow solid was target compound 1-4.

Mass analysis (FDMS): 487 (M$^+$)
Elemental analysis (calculated): C=91.1, H=6.0 and N=2.9
Elemental analysis (found): C=91.1, H=6.1 and N=2.8

Example 2

Synthesis of Compound 1-14

In a nitrogen atmosphere, a 300 ml flask equipped with a stirrer was charged with 11.1 g (40 mmol) of the compound A, obtained in Synthesis Example 1, 1.9 g (20 mmol) of aniline (available from Wako Pure Chemical Industries Ltd.), 4.8 g (50 mmol) of sodium-tert-butoxide (available from Kishida Chemical Co., Ltd.), 225 mg (1.0 mmol) of palladium acetate (available from Kishida Chemical Co., Ltd.), 0.8 g (4.0 mmol) of tri-tert-butylphosphine (available from Aldrich Chemical Co., Inc.) and 100.0 g of o-xylene (available from Kishida Chemical Co., Ltd.). The charged mixture was stirred at 140° C. for 15 hours. After completion of the reaction, 30 ml of distilled water was added to the reaction solution, and the reaction mixture was stirred at room temperature for 0.5 hour and allowed to leave to effect phase separation. An aqueous phase was removed. Then an obtained organic layer was washed with an aqueous saturated sodium chloride solution, and an aqueous phase was removed. Then an obtained organic layer was concentrated under a reduced pressure and o-xylene as solvent was distilled off. The thus-obtained residue was subjected to silica gel column chromatography to give 10.2 g of a light yellow solid with a purity of 99.9% in a yield of 88%.

Mass analysis and elemental analysis revealed that the obtained light yellow solid was target compound 1-14.

Mass analysis (FDMS): 577 (M$^+$)
Elemental analysis (calculated): C=91.5, H=6.1 and N=2.4
Elemental analysis (found): C=91.5, H=6.0 and N=2.5

Example 3

Synthesis of Compound 1-16

The procedures described in Example 2 were repeated wherein 2.1 g (20 mmol) of p-aminotoluene (available from Wako Pure Chemical Industries Ltd.) was used instead of 1.9 g (20 mmol) of aniline (available from Wako Pure Chemical Industries Ltd.) with all other procedures remaining the same. Thus 10.1 g of a light yellow solid with a purity of 99.9% was obtained in a yield of 85%.

Mass analysis and elemental analysis revealed that the obtained light yellow solid was target compound 1-16.

Mass analysis (FDMS): 591 (M$^+$)
Elemental analysis (calculated): C=91.3, H=6.3 and N=2.4
Elemental analysis (found): C=91.4, H=6.2 and N=2.4

Example 4

Synthesis of Compound 1-18

The procedures described in Example 2 were repeated wherein 1.9 g (20 mmol) of 4-aminopyridine (available from Wako Pure Chemical Industries Ltd.) was used instead of 1.9 g (20 mmol) of aniline (available from Wako Pure Chemical Industries Ltd.) with all other procedures remaining the same. Thus 10.0 g of a light yellow solid with a purity of 99.9% was obtained in a yield of 87%.

Mass analysis and elemental analysis revealed that the obtained light yellow solid was target compound 1-18.

Mass analysis (FDMS): 578 (M$^+$)
Elemental analysis (calculated): C=89.2, H=5.9 and N=4.8
Elemental analysis (found): C=89.0, H=6.0 and N=4.9

Reference Example 1

Synthesis of Comparative Compound M1

The procedures described in Example 2 were repeated wherein 6.7 g (20 mmol) of N,N'-diphenylbenzidine (available from Aldrich Chemical Co., Inc.) was used instead of 1.9 g (20 mmol) of aniline (available from Wako Pure Chemical Industries Ltd.) with all other procedures remaining the same. Thus 14.0 g of a light yellow solid with a purity of 99.9% was obtained in a yield of 85%.

Mass analysis and elemental analysis revealed that the obtained light yellow solid was the comparative compound M1.

Mass analysis (FDMS): 820 (M$^+$)
Elemental analysis (calculated): C=90.7, H=5.9 and N=3.4
Elemental analysis (found): C=90.7, H=6.0 and N=3.3

Comparative compound M1

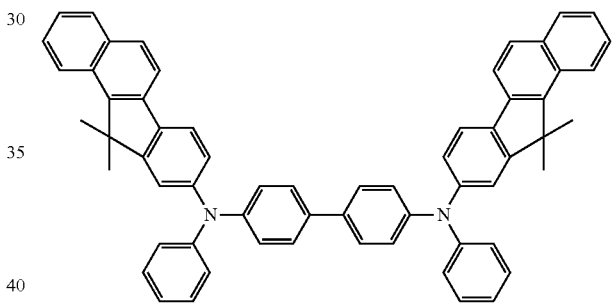

HOMO (eV), LUMO (eV), glass transition temperature (° C.), sublimation temperature (° C.) and decomposition temperature (° C.) of the compounds 1-4, 1-14, 1-16 and 1-18, obtained in Examples 1 to 4, and comparative compound M1 obtained in Comparative Example 1 were measured. The results are shown in Table 1.

For comparison, HOMO (eV), LUMO (eV), glass transition temperature (° C.) and sublimation temperature (° C.) of α-NPD (4,4'-bis[N-(1-naphthyl)-N-phenylamino]biphenyl), which is well known as an organic electroluminescent material, were also measured. The results are also shown in Table 1.

TABLE 1

| Compound | HOMO (eV) | LUMO (eV) | Glass Transition temp. (° C.) | Sublimation temp. (° C.) | Decomposition temp. (° C.) |
|---|---|---|---|---|---|
| 1-4 | −5.5 | −2.4 | 88 | 210 | 340 |
| 1-14 | −5.5 | −2.4 | 130 | 240 | 340 |
| 1-16 | −5.4 | −2.4 | 130 | 280 | 340 |
| 1-18 | −5.7 | −2.5 | 135 | 260 | 340 |
| α-NPD | −5.5 | −2.4 | 96 | 300 | — |
| M1 | −5.4 | −2.5 | 154 | 330 | 340 |

Example 5

Manufacture of Organic Electroluminescent Device and Evaluation Thereof

A glass substrate with an indium-tin oxide (ITO) transparent electrode having a stripe pattern comprised of ITO film strips each having a 2 mm width was prepared. The substrate was washed with acetone and then with isopropyl alcohol, while being irradiated with ultrasonic wave. The substrate was further washed with boiling isopropyl alcohol, and then dried. The dried substrate was surface-treated with by irradiation of ultraviolet rays and generation of ozone to prepare a transparent electrically conductive glass substrate.

The thus-treated glass substrate was placed in a vacuum deposition chamber, and the inner pressure was reduced to $1.0 \times 10^{-4}$ Pa. Phthalocyanine copper was vacuum-deposited on the transparent ITO electrode to form a hole injection layer with a thickness of 25 nm.

Then the compound 1-14, synthesized in Example 2, was vacuum-deposited on the hole injection layer to form a hole transport layer with a thickness of 45 nm. Then aluminum trisquinolinol complex was vacuum-deposited on the hole transport layer to form a luminous-and-electron-transport layer with a thickness of 60 nm. Thereafter LiF and Al were deposited into film thicknesses of 0.5 nm and 100 nm, respectively, to form a LiF—Al metal electrode. The film thicknesses were measured by a stylus profile measuring instrument DEKTAK. Then the thus-obtained substrate assembly with multi-layers was placed in a globe box filled with a nitrogen gas having an oxygen-and-moisture content of below 1 ppm, wherein the assembly was encapsulated with a glass cap and a ultraviolet ray-curable epoxy resin available from Nagase Chemtex Corporation. Luminous properties of the thus-manufactured organic electroluminescent device were evaluated by using a luminance meter BM-9 available from Topcon Corporation while direct current was applied to the device with the ITO electrode as cathode and the LiF—Al metal electrode as anode. The evaluation of the luminous properties was conducted at a current density of 20 mA/cm$^2$ by measuring working voltage (V), luminance (cd/m$^2$), current efficiency (cd/A) and power efficiency (1 m/W). The evaluation results are shown in Table 2, below.

Example 6

Manufacture of Organic Electroluminescent Device and Evaluation Thereof

By the same procedures as described in Example 5, an organic electroluminescent device was manufactured wherein the compound 1-16, synthesized in Example 3, was used instead of the compound 1-14, synthesized in Example 2, for the formation of a hole transport layer. All other procedures remained the same.

The luminous properties of the device were evaluated by the same methods as adopted in Example 5. The working voltage, luminance, current efficiency and power efficiency, as measured at a current density of 20 mA/cm$^2$, are shown in Table 2, below.

Comparative Example 1

Manufacture of Organic Electroluminescent Device and Evaluation Thereof

By the same procedures as described in Example 5, an organic electroluminescent device was manufactured wherein α-NPD was used instead of the compound 1-14, synthesized in Example 2, for the formation of a hole transport layer. All other procedures remained the same.

The luminous properties of the device were evaluated by the same methods as adopted in Example 5. The working voltage, luminance, current efficiency and power efficiency, as measured at a current density of 20 mA/cm$^2$, are shown in Table 2, below.

Comparative Example 2

Manufacture of Organic Electroluminescent Device and Evaluation Thereof

By the same procedures as described in Example 5, an organic electroluminescent device was manufactured wherein the comparative compound M1, synthesized in Reference Example 1, was used instead of the compound 1-14, synthesized in Example 2, for the formation of a hole transport layer. All other procedures remained the same.

The luminous properties of the device were evaluated by the same methods as adopted in Example 5. The working voltage, luminance, current efficiency and power efficiency, as measured at a current density of 20 mA/cm$^2$, are shown in Table 2, below.

TABLE 2

| Examples | Compound for hole Transport layer | Working Voltage (V) | Luminance (cd/m$^2$) | Current efficiency (cd/A) | Power efficiency (lm/W) |
| --- | --- | --- | --- | --- | --- |
| Example 5 | 1-14 | 4.8 | 1050 | 4.6 | 2.9 |
| Example 6 | 1-16 | 5.0 | 1035 | 4.7 | 2.9 |
| Comp. Ex. 1 | α-NPD | 5.0 | 978 | 4.0 | 2.5 |
| Comp. Ex. 2 | M1 | 4.8 | 858 | 4.0 | 2.6 |

INDUSTRIAL APPLICABILITY

The amine derivative according to the present invention can be operated with a low working voltage and exhibits high power efficiency as compared with the conventional materials. Therefore, the amine derivative is suitable for a hole injection material, a hole transport material and a luminous material, which are used in an organic electroluminescent device and an electrophotographic photoreceptor and other devices. Especially, when the amine derivative is used as a hole transport material, it is expected to be operated with a low working voltage and an enhanced power efficiency as compared with the conventional materials.

Further the amine derivative can be used as organic photoconducting materials for opto electronic devices, solar cells and image sensors.

The invention claimed is:

1. An amine derivative represented by the following general formula (1) and exhibiting a temperature difference of 30° C. or more as defined by the difference of decomposition temperature (° C.) minus sublimation temperature (° C.):

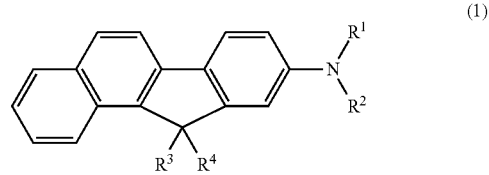

(1)

wherein
- R¹ and R² may be the same or different and independently represent an aryl group having 6 to 18 carbon atoms, which may have a substituent or substituents which are an alkyl group having 1 carbon atom or a heteroaryl group having 5 carbon atoms, which may have a substituent or substituents which are an alkyl group having 1 carbon atom, provided that one of R¹ and R² is an aryl group having 12 to 18 carbon atoms, which may have a substituent or substituents which are an aryl group having 1 carbon atom; and
- R³ and R⁴ may be the same or different and represent a hydrogen atom or an alkyl group having 1 carbon atom.

2. An organic electroluminescent device comprising at least one layer selected from an emitting layer, a hole transport layer and a hole injection layer, which layers are made of the amine derivative as claimed in claim 1.

3. A process for producing an organic electroluminescent device comprising making at least one layer selected from an emitting layer, a hole transport layer and a hole injection layer, wherein said at least one layer is made by forming a thin film by a vacuum deposition method from the amine derivative as claimed in claim 1.

4. The amine derivative according to claim 1, which is selected from those represented by the following formulas:

1-4

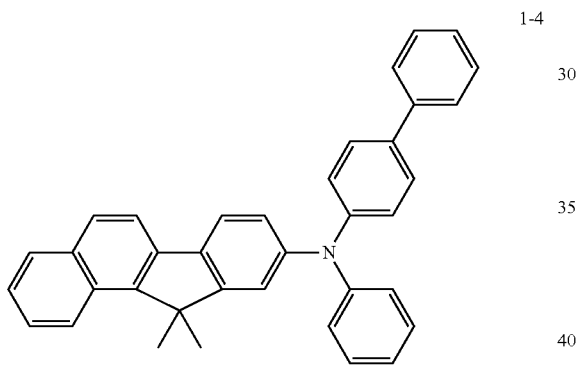

1-5

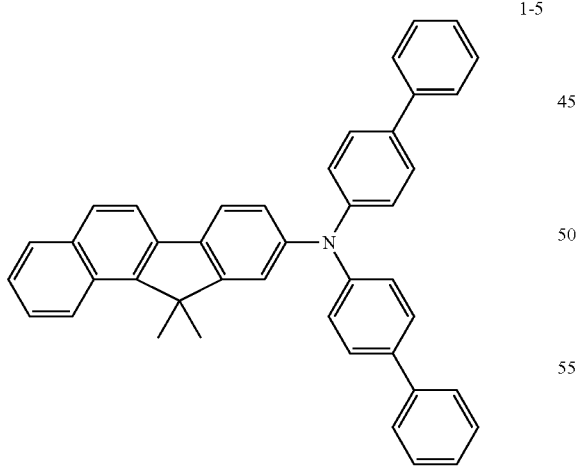

1-14

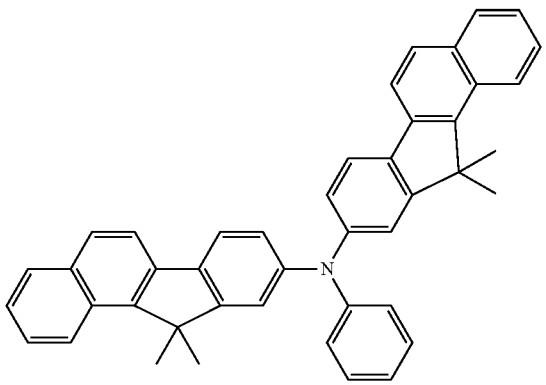

1-16

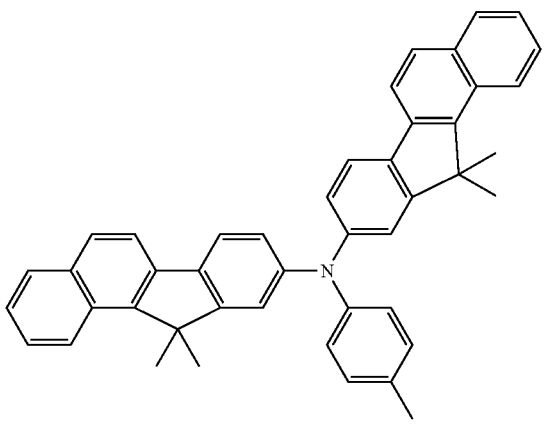

1-18

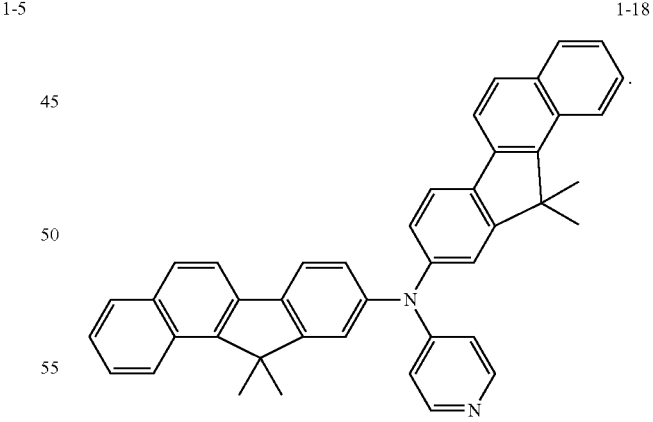

* * * * *

UNITED STATES PATENT AND TRADEMARK OFFICE
CERTIFICATE OF CORRECTION

| | | |
|---|---|---|
| PATENT NO. | : 8,846,214 B2 | Page 1 of 1 |
| APPLICATION NO. | : 13/375997 | |
| DATED | : September 30, 2014 | |
| INVENTOR(S) | : S. Ishikawa et al. | |

It is certified that error appears in the above-identified patent and that said Letters Patent is hereby corrected as shown below:

In the Claims,

Claim 1 (col. 19, line 10) please change "aryl" to --alkyl--.

Signed and Sealed this
Twenty-first Day of July, 2015

Michelle K. Lee
*Director of the United States Patent and Trademark Office*